(12) United States Patent
Zukoski et al.

(10) Patent No.: US 10,479,028 B2
(45) Date of Patent: Nov. 19, 2019

(54) SYSTEM AND METHOD FOR MAKING SOCKETS FOR PROSTHETIC LIMBS

(71) Applicant: 3D Systems, Inc., Rock Hill, SC (US)

(72) Inventors: Andrew Zukoski, Berkeley, CA (US); Andrew Miller, Oakland, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 468 days.

(21) Appl. No.: 14/728,044

(22) Filed: Jun. 2, 2015

(65) Prior Publication Data
US 2015/0352793 A1    Dec. 10, 2015

Related U.S. Application Data

(60) Provisional application No. 62/007,466, filed on Jun. 4, 2014.

(51) Int. Cl.
| | |
|---|---|
| *A61F 2/50* | (2006.01) |
| *A61F 2/80* | (2006.01) |
| *B33Y 50/02* | (2015.01) |
| *B29C 67/00* | (2017.01) |
| *B29C 64/386* | (2017.01) |
| *G05B 19/4099* | (2006.01) |
| *B33Y 80/00* | (2015.01) |

(52) U.S. Cl.
CPC ........ *B29C 67/0088* (2013.01); *A61F 2/5044* (2013.01); *A61F 2/80* (2013.01); *B29C 64/386* (2017.08); *B33Y 50/02* (2014.12); *B33Y 80/00* (2014.12); *G05B 19/4099* (2013.01); *G05B 2219/35134* (2013.01)

(58) Field of Classification Search
USPC ........................................................ 623/901
See application file for complete search history.

(56) References Cited

U.S. PATENT DOCUMENTS

| | | | | |
|---|---|---|---|---|
| 5,824,111 | A * | 10/1998 | Schall | A61F 2/5046 264/40.1 |
| 6,144,386 | A * | 11/2000 | Pratt | A61B 5/1077 345/419 |
| 6,463,351 | B1 * | 10/2002 | Clynch | A61F 2/5046 623/901 |
| 7,357,636 | B2 * | 4/2008 | Hedge | A61C 7/08 433/24 |
| 2005/0119777 | A1 * | 6/2005 | Arbogast | A61F 2/5046 700/117 |

(Continued)

OTHER PUBLICATIONS

PCT International Search Report the International Searching Authority for PCT/US2015/033664, dated Jun. 2, 2015 (4 pages).

(Continued)

*Primary Examiner* — Jeffrey M Wollschlager
*Assistant Examiner* — Armand Melendez
(74) *Attorney, Agent, or Firm* — Staniford Tomita LLP

(57) ABSTRACT

A socket for a prosthetic limb is created by making a cast of a residual limb. Marks can be applied to the interior surface of the cast to indicate the locations of anatomical features of the residual limb. The marked interior surface can be scanned and the scan data can be sent to a master fabrication center. The scan data can be modified and a master can be produced from the modified scan data. The socket can then be formed from the plastic material on the master.

7 Claims, 11 Drawing Sheets

(56) References Cited

U.S. PATENT DOCUMENTS

2006/0179935 A1    8/2006  Warila
2009/0299490 A1  12/2009  Summit
2010/0161076 A1    6/2010  Pallari
2011/0004335 A1*  1/2011  Summit ................ A61F 2/5046
                                                                         700/119

OTHER PUBLICATIONS

PCT Written Opinion of the International Searching Authority for PCT/US2015/033664, dated Jun. 2, 2015 (5 pages).

* cited by examiner

SYSTEM AND METHOD FOR MAKING SOCKETS FOR PROSTHETIC LIMBS

CROSS REFERENCE TO RELATED APPLICATIONS

This application claims priority to U.S. Provisional Patent Application No. 62/007,466, "System And Method For Making Sockets For Prosthetic Limbs" filed Jun. 4, 2014 which is hereby incorporated by reference in its entirety.

BACKGROUND

A prosthesis limb replaces a missing extremity, such as an arm or a leg and may be needed for a variety of reasons, including diseases, and accidents. An artificial limb may also be needed when a person is born with a missing or damaged limb(s). The type of prosthesis limb used is determined largely by the extent of an amputation or loss and location of the missing limb. A transtibial prosthesis is an artificial leg that is attached to a user below the knee and includes a lower leg, ankle and foot. The transfemoral prosthesis is an artificial leg that is attached to the user's amputated limb above the knee and includes an upper leg and mechanical knee. A transradial prosthesis is an artificial arm that is attached to the user below the elbow and includes a forearm and hand. A transhumeral prosthesis is an artificial arm that is attached to the user above the elbow.

In developing areas of the world, including large portions of Africa, the leading causes of amputations are industrial, vehicular, and war related accidents. In more developed areas, such as North America and Europe, the leading causes for the amputations are diseases including cancer, infection and circulatory. In the United States, approximately 100,000 legs are lost each year to diabetes, vascular disorder, accidents and cancer. Because there are so many amputations, there is a substantial need for prosthetic limbs.

SUMMARY OF THE INVENTION

The present invention is directed towards method for creating a socket for a prosthetic device. A socket for a prosthetic limb can be created by making a cast of a residual limb. The cast can be formed by placing a cast material around the residual limb of the patient. The cast material can harden around the residual limb and a first cast can be removed from the residual limb. The marks can be applied to the interior surface of the first cast to indicate the locations of anatomical features of the residual limb. The marked interior surface can be scanned and the scan data can be sent to a master fabrication center. The scan data can be modified and a second cast can be produced from the modified scan data.

In an embodiment, the second cast can be fabricated from the modified scan data with a 3D printer which can deposit a plurality of parallel planar layers of material. Each layer deposited by the 3D printer forms a cross section of the master. Each layer is fused to the adjacent layer and the 3D printed master can be made of a homogeneous material. In other embodiments, the master can be fabricated from the modified scan data using different fabrication processes. For example, the second cast can be made of plaster from the first cast.

The second cast can match a surface of a residual limb of a patient prior to modification. The second cast can be modified to create a master. Material can be removed from the second cast or additional material can be added to the surface topography based on the anatomical references on the master. When material is added, the outer surface of the second cast will expand outward beyond the matching surface of the residual limb. When material is removed, the outer surface of the second cast will contract inward from the matching surface of the residual limb. The surface modifications can be applied to the second cast according to a recipe. For example material can be added or removed based upon the anatomic locations of bone, nerves, blood vessels, scar tissue or other body features. However, in some embodiments, some changes made to the second cast are idiosyncratic, based on the specifics of the patient and/or preferences of the clinician. The modified second cast can be a master.

The socket can then be formed from the plastic material using the master. In an embodiment, the socket can be made from a sheet of thermo-plastic material. The material can be heated and formed around the master. In an embodiment, a vacuum forming process can be used to conform the thermo-plastic material to the master. The molded thermo-plastic material can be trimmed to create the socket and attached to a prosthetic device.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
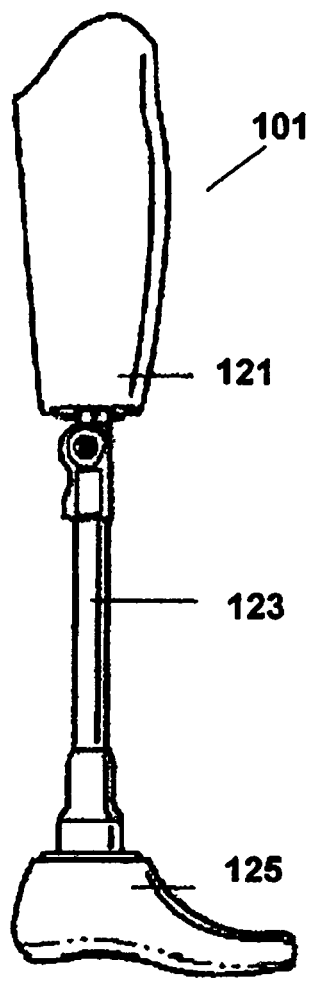
FIG. 1 illustrates a side view of an embodiment of a prosthetic leg.

The engineering of prosthetic limbs has improved greatly. In particular, artificial knees and feet have been developed for prosthetic legs that provide increased mobility and functionality. With reference to FIG. 1, a prosthetic leg 101 is shown having a socket 121 that has a recessed surface that engages the end of the user's amputated leg. The socket 121 is typically a padded plastic structure that distributes the compression forces on the end of the residual limb. The bottom of the socket 121 is attached to a pylon 123 which is a tubular support that can be made of titanium or aluminum. The pylon can be manufactured through an extrusion process. The bottom of the pylon 123 is attached to an artificial foot 125 that can be a molded plastic structure. The various socket 121, pylon 123 and foot 125 can be coupled together using fasteners including bolts, screws and adhesives.

Figure 2:
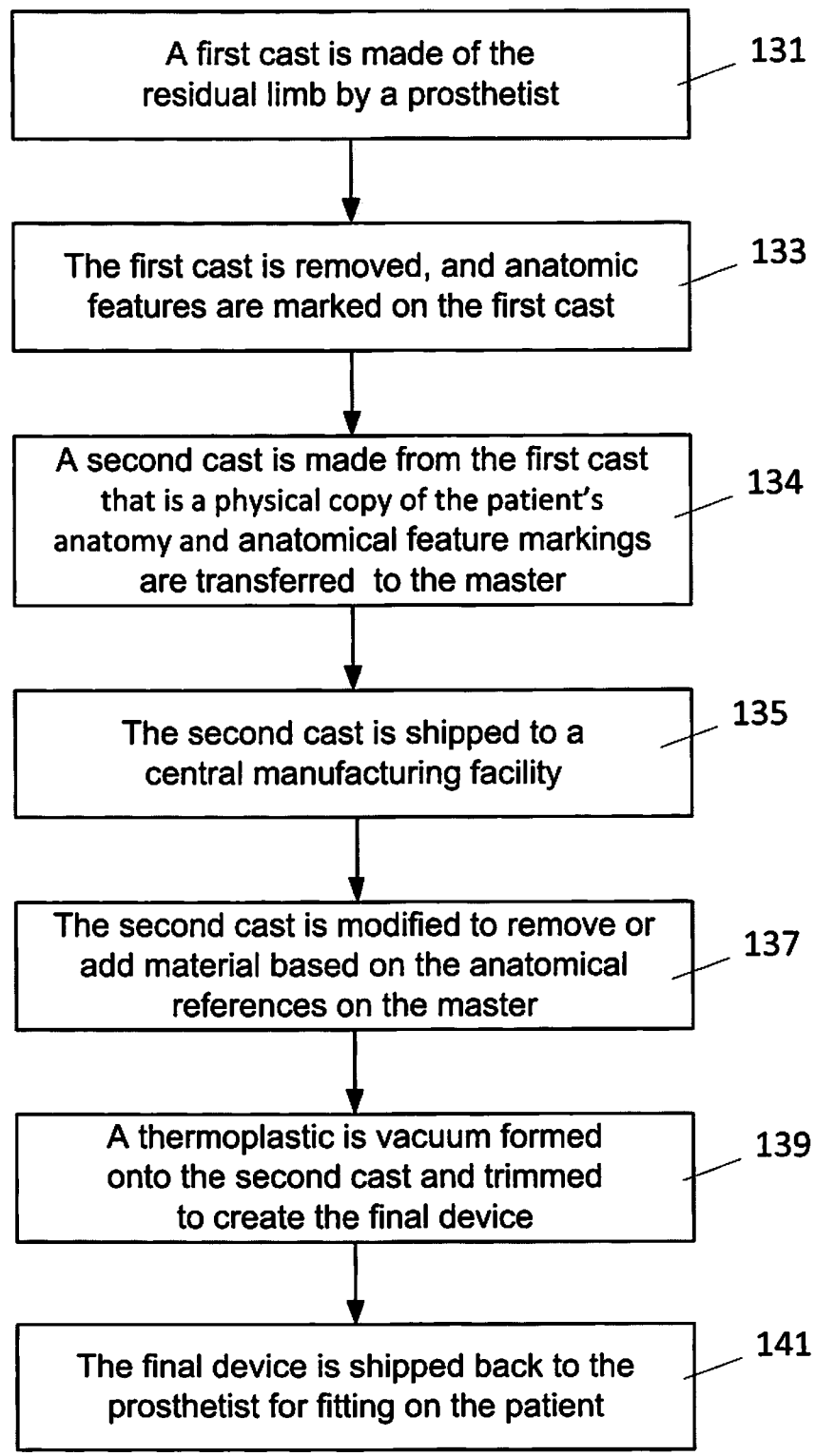
FIG. 2 illustrates a first embodiment of flowchart for processes for fabricating prosthetic sockets.
Figure 6:
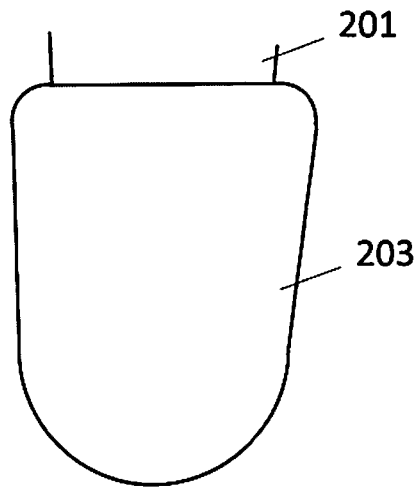
FIG. 6 illustrates a side view of an embodiment of a cast formed on a residual limb.
Figure 7:
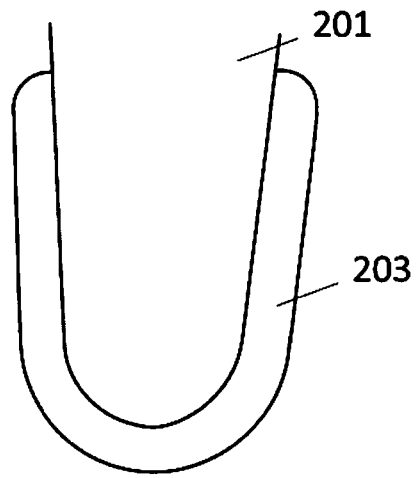
FIG. 7 illustrates a side view of an embodiment of a cast formed on a residual limb.

Many custom prosthetic sockets and ankle-foot orthosis (AFO) are fabricated with a complex, ad-hoc, multi-step process. With reference to FIG. 2, below is a possible workflow for fabricating prosthetic sockets:

1) A first cast is made of the residual limb or lower limb by a prosthetist (FIG. 2, 131). With reference to FIGS. 6 and 7, the first cast 203 can be made from a cotton bandage that has been combined with plaster of Paris, which is placed on the residual limb 201 and contacts all exposed surfaces of the residual limb 201. The first plaster cast 203 hardens on the after it has been made wet. The residual limb 201 may have a plurality of anatomic features that are important to fit of the socket on the patient. These anatomic features may or may not have identifiable topographic features.

In an embodiment a prosthetist might deform the first plaster cast to modulate compression locally corresponding to a plurality of anatomic features and considerations for fit of the socket. One deformation the prosthetist might make is compression on the lateral aspects and elongation on the ventral and dorsal aspects of the cast to create an oblong shape to prevent axial rotation of the socket about the residual limb. In an embodiment, this deformation can be described as "rectangularization" to lower socket to reduce the potential for rotation of the socket on the residual limb.

It is also possible to create other adjustments so that the topography of the first plaster cast does not exactly match or correspond as an opposite mold of the surface of the residual limb. In other embodiments, the first cast can be made of any other suitable material. The first cast can be made in the office of the prosthetist.

Figure 8:
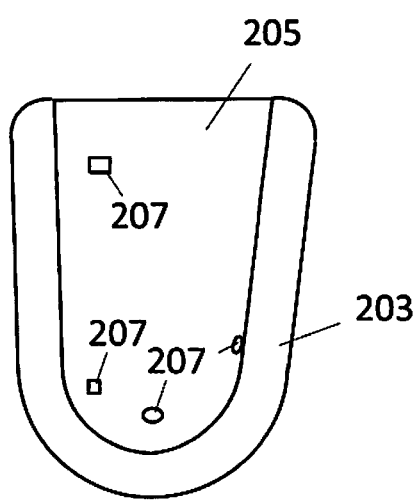
FIG. 8 illustrates a side view of an embodiment of a cast having internal markings.

2) The first cast can be removed from the patient's residual limb (FIG. 2, 133). With reference to FIG. 8, the interior surfaces 205 of the first cast can provide an exact match or mold of the topography of the residual limb. As discussed, the residual limb may have a plurality of anatomic features. Markings or points 207 can be created on the interior surfaces 205 of the first cast 203 that correspond to or are adjacent to these anatomic features. In other embodiments, the exterior outer surfaces of the cast can be annotated with markings or points 207. These markings or points 207 can be added to the inner generally concave surfaces and/or outer surfaces of the plaster cast 203. These markings 207 can be stickers, ink markings, etc.

Figure 10:
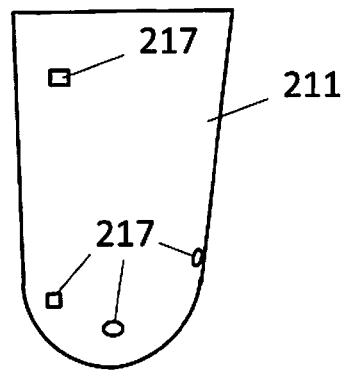
FIG. 10 illustrates an embodiment of a master with markings.

3) With reference to FIG. 10, a second cast 211 can be made from the first cast (FIG. 2, 134). The second cast 211 can be made of plaster with wet plaster soaked cotton bandages placed over all interior surfaces of the first cast. The markings 217 from the first cast indicating the anatomical features can be transferred to the second cast 217 or "master" that is substantially an exact copy of the patient's residual limb anatomy.

4) The second cast can then be shipped to a central manufacturing facility (FIG. 2, 135).

5) Craftsmen at the central manufacturing facility can then modify the second plaster cast to create a master, removing material from the second cast or adding additional material to the second cast to the surface topography based on the anatomical references on the master. (FIG. 2, 137) The second cast can match a surface of a residual limb of a patient prior to modification. When material is added, the outer surface of the second cast will expand outward beyond the matching surface of the residual limb. When material is removed, the outer surface of the second cast will contract inward from the matching surface of the residual limb. Most of these surface modifications are according to a recipe. For example material can be added or removed based upon the anatomic locations of bone, nerves, blood vessels, scar tissue or other body features. However, in some embodiments, some changes made to the second cast are idiosyncratic, based on the specifics of the patient and/or preferences of the clinician.

Figure 15:
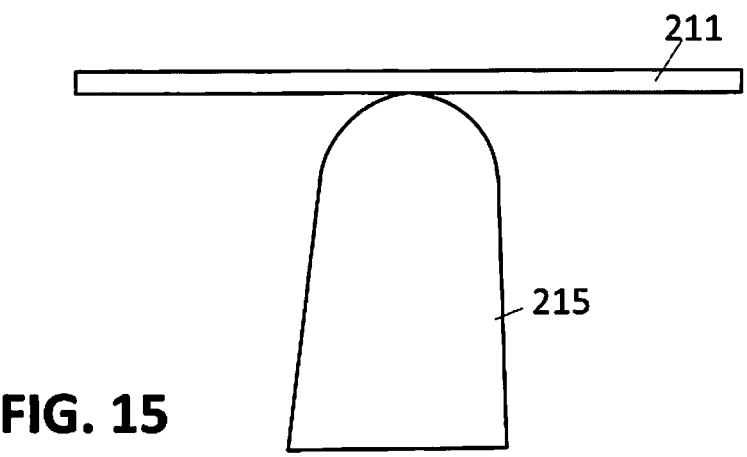
FIG. 15 illustrates an embodiment of a thermoplastic sheet placed on a master.
Figure 16:
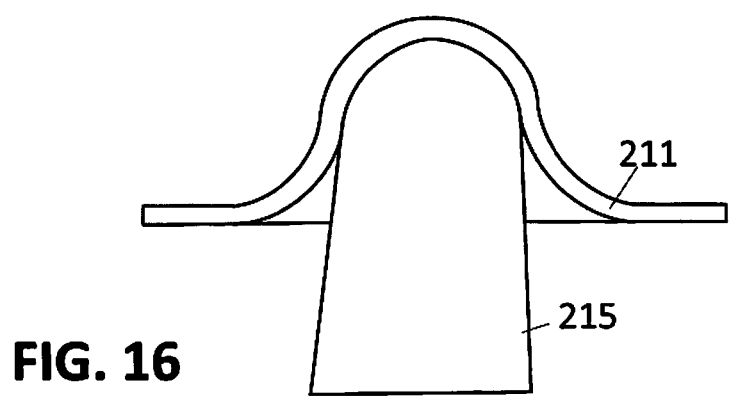
FIG. 16 illustrates an embodiment of a thermoplastic sheet partially molded around a master.
Figure 17:
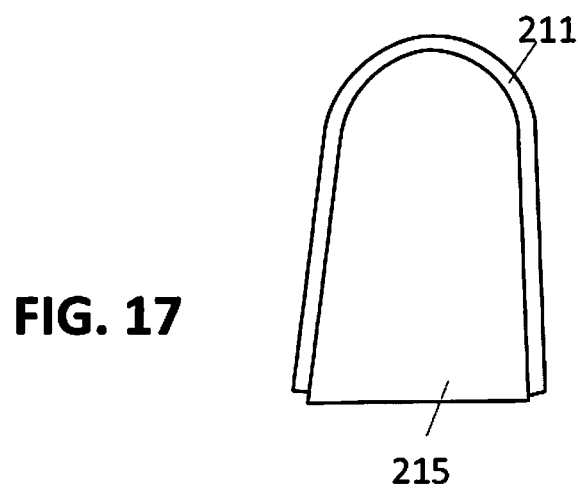
FIG. 17 illustrates an embodiment of a thermoplastic sheet deformed molded a master.

6) With reference to FIGS. 15-17, a thermoplastic can be vacuum-formed onto the second cast/master and trimmed to create the final socket device (FIG. 2,139). In an embodiment, a sheet of thermoplastic material can be heated to soften the material and molded around the second cast. The thermoplastic material can be vacuum formed around the second cast with a vacuum applied to the inner surface of the thermoplastic material to cause the thermoplastic material to form to the second cast.

Figure 18:
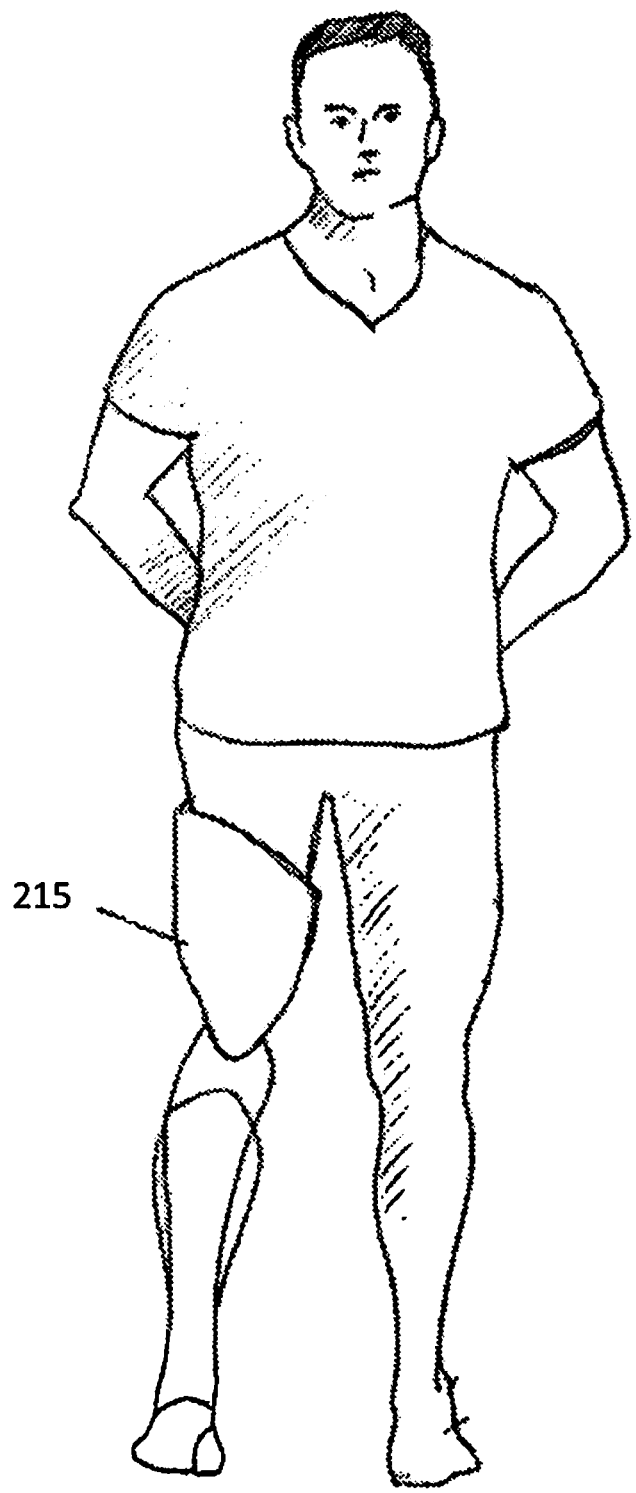
FIG. 18 illustrates an embodiment of a prosthetic leg worn by a patient.

7) With reference to FIG. 18, the socket device can then be shipped back to the prosthetist office for fitting on the patient's residual limb and connection to the prosthetic limb 215. (FIG. 2, 141).

Figure 3:
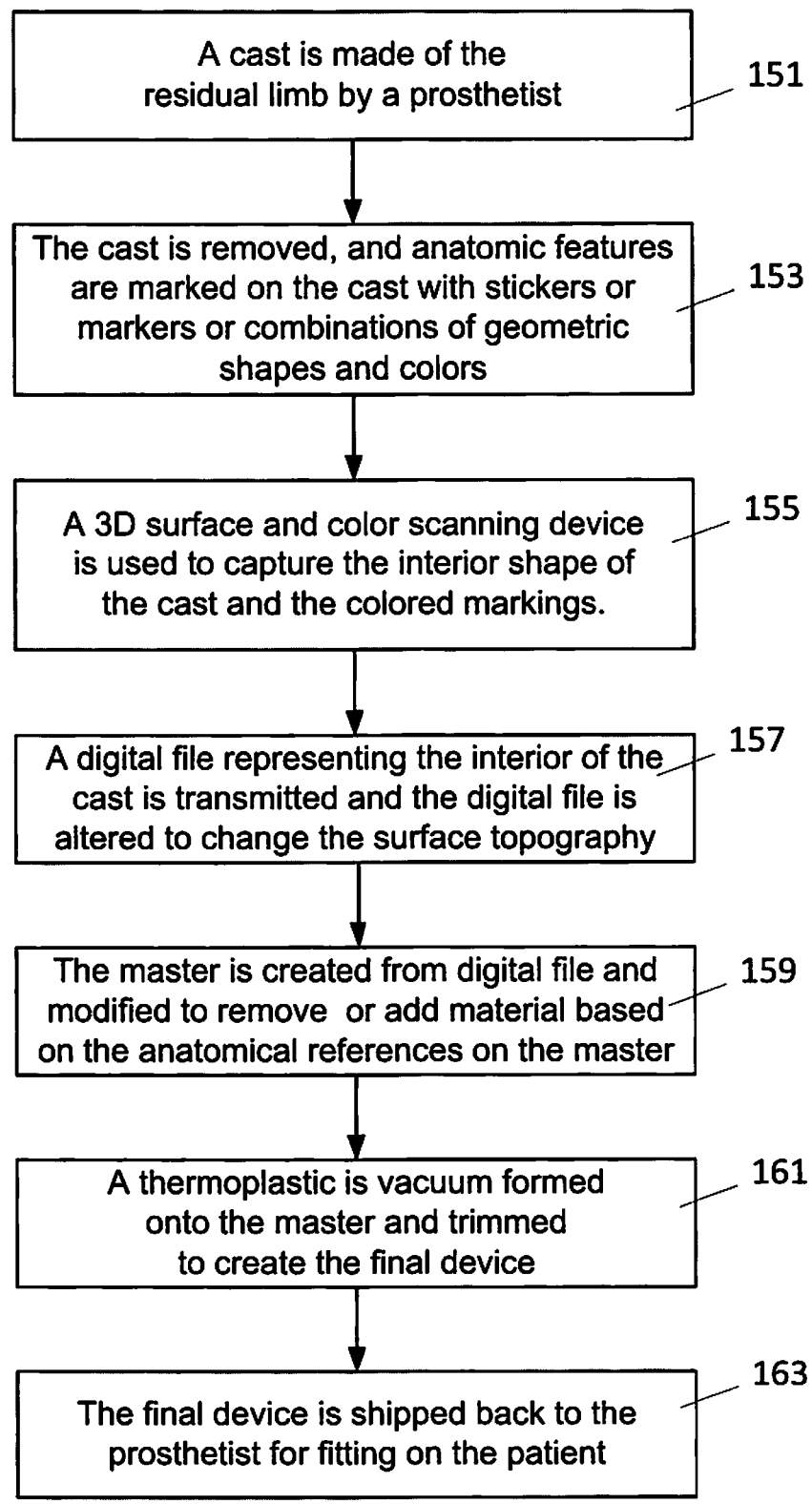
FIG. 3 illustrates a second embodiment of flowchart for processes for fabricating prosthetic sockets.

In an embodiment, it may be possible to improve upon the described process with an improved process which can reduce or eliminate the cost and time associated with shipping the plaster master described above. With reference to FIG. 3, the alternative process can reduce the amount of time that must be spent manually modifying the plaster master in step 159. Each of the process steps are disclosed below.

1) With reference to FIGS. 6 and 7, a first cast 203 is made of the residual limb/lower limb 201 by a prosthetist in their office or other service provider. This can be substantially the same process as step 1 described above (FIG. 3, 151). In an embodiment, it is possible to mark the patient's residual limb and have these markings transferred to the first cast 203. In yet another embodiment, it can be possible to mark the patient's residual limb, scan the residual limb with markings, and register the markings to the scan of the first cast 203. In this embodiment, the annotations can be digitally transferred from the residual limb to the computer model of the first cast 203. In an embodiment, the scan data can be obtained with a plurality of cameras using a photogrammetry process which is described in U.S. Pat. No. 8,005,651, "Custom Braces, Casts And Devices And Methods For Designing And Fabricating US Patent Application" which is hereby incorporated by reference in its entirety.

2) With reference to FIG. 8, the first cast 203 is removed from the patient's residual limb or lower limb, and anatomic features are marked on the first cast (FIG. 3, 153). The markings 207 can be stickers or markers or other combinations of shapes and colors to indicate geometry and/or design intent. The color, shape or any other distinctive features of the markings can indicate specific types of anatomic features. For example, circles or black markings can represent surfaces close to bone and triangular or red markings can represent nerve bundles. The markings 207 can correspond to anatomy and the locations of anatomical features of the residual limb. The markings 207 can also provide information for modification of the first cast 203. In different embodiments, some of the markings 207 can give instructions to persons later in the fabrication process. For example, if the markings 207 include a blue curved region and a red curved region, these markings 207 may indicate that everything inside the blue curve is sanded down 2 mm while everything inside a red region marked by a curve should be raised 2 mm. In other embodiments, the markings 207 can be used to indicate various other modifications to the first cast 203.

Figure 9:
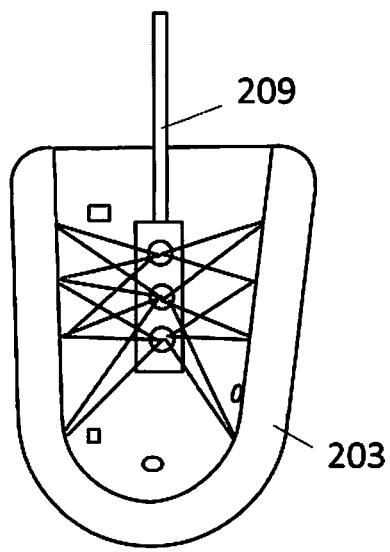
FIG. 9 illustrates a side view of an embodiment of a cast with a scanner for detecting the internal surface of the cast and internal markings.

3) With reference to FIG. 9, a 3D scanning device 209 can be used to capture the interior shape or exterior shape of the first cast 203 and the colored markings 207 (FIG. 3, 155). The first cast 203 has an interior surface 205 that is concave. The important topography surfaces of the first cast 203 are within the interior open volume of the first cast 203. In an embodiment, the 3D scanner 209 can be placed within the first cast 209 and may be moved across the interior surface topography. Alternatively, interior surfaces of the first cast can be scanned by holding the scanner a distance from the first cast 203 and rotating the angle of incidence between the scanner and the first cast 203. In other embodiments, any other suitable scanning methods can be used.

A single or a plurality of scanners 209 can be used to capture surface data for the interior surface topography. Various scanning mechanisms can be used to record the surface data. For example, a photogrammetry system can be used to capture color and depth data simultaneously. Alternatively, a time-of-flight sensor augmented with color sensor can be used to record the surface topography and color data. A structured light sensor can also be used to capture depth and color data simultaneously. The structured light sensor can also capture depth data and can be augmented with a color sensor(s) to capture the colored markings. A laser scanner can also be used to capture depth data and this surface topography data can be augmented with color sensor(s) to capture the colored markings. The scanner data and color sensor data can then be processed by a computer to create a digital representation of the first cast together with the markings 207 applied to the first cast 203.

4) The digital representation of the first cast 203 can be transmitted off-site and the interior surfaces can be converted into outer surfaces (FIG. 3, 157). This can be considered a digital representation of the negative space of the first cast 203. The digital representation can match the digital representation of the residual limb of the patient.

Figure 14:
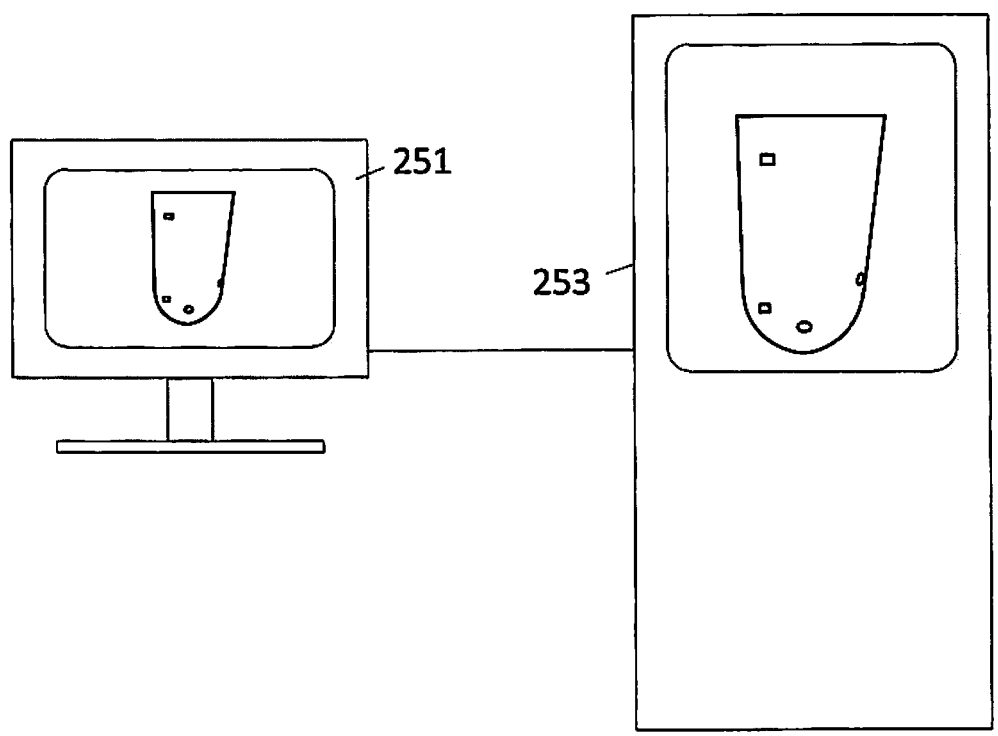
FIG. 14 illustrates an embodiment of a computer aided design (CAD) device for applying deformations to the digital representation of the first cast.

With reference to FIG. 14, in an embodiment, a recipe of "deformations" can be digitally applied. For example material can be added or removed based upon the anatomic locations of bone, nerves, blood vessels, scar tissue or other body features. However, in some embodiments, some changes made idiosyncratic for the patient, based on the specifics of the patient and/or preferences of the clinician.

In one embodiment, the deformation can be described as inflations and deflations with inflations representing expanded or inflated deformations relative to the actual measured surface topographies. The deflations representing compressed or deflated deformations compared to the actual measured surface topographies 203. By adding inflation and deflation deformations, the pressure applied to the residual limb from the socket worn on the limb can be intentionally non-uniform. For example, the inflation and deflation deformations of the mold can increase weight bearing on soft tissue surfaces of the residual limb and decrease the pressure and force on more sensitive anatomical components of the residual limb such as nerve bundles and residual bone. Deformations can also be used to smooth the surface topography of the mold to reduce irregularities in the resulting devices such as sockets. The inflations and deflations can also be used to accommodate any intermediate devices that may be placed between the residual limb and the socket of the prosthetic such as padding, sensors, etc. These deformations can be partially or completely applied digitally, meaning that a person operating the computer aided design (CAD) device 251 can apply some or all of the deformations to the digital representation of the first cast. In an embodiment, the deformations can be applied automatically with software on that manual operation is no longer needed. The digital representation of the first cast with applied deformation modifications can be used to create a final digital representation which can correspond to or closely resemble the patient's residual limb. More specifically, the digital representation matches the residual limb with the exception of the inflations and/or deflations which are mismatched surface areas of the digital representation.

5) The final digital representation can be used to create a modified shape "master" that can be fabricated out of a plaster-like material in a central manufacturing facility (FIG. 3, 159). For example, the master can be made of gypsum using an additive manufacturing process. In one embodiment, a 3D printer that prints in a sandstone or sandstone like material can be used and the printed object is suitably similar to a plaster master made from the cast. This object is a physical representation of a modified patient's residual limb. With reference to FIG. 14, in an embodiment, the master can be fabricated with a 3D printer 253 using the CAD data. The master can be formed by creating a plurality of planar layers where each layer represents a cross section of the master. The planar layers can be sequentially bonded to the prior formed planar layer and the bonded planar layers form the master. Thus, each of the planar layers are parallel to each other.

In yet another embodiment, it may be possible to create a master based upon a direct scan of the patient's residual limb rather than scans of casts made from the residual limb. This process is described with reference to FIGS. 5 and 10-16.

6) Craftsmen can then apply any further idiosyncratic modifications to surface topography of this printed master. In yet other embodiments, a test socket can be made from the 3D printed master. The test socket can be formed by creating a plurality of planar layers where each layer represents a cross section of the test socket. The planar layers can be sequentially bonded to the prior formed planar layer and the bonded planar layers form the test socket. The test socket can be modified and a cast can be made from the test socket. The final socket product can then be made from a master poured into that cast.

7) With reference to FIGS. 15-17, a thermoplastic material can be vacuum-formed onto the master and trimmed to create the final socket device. In an embodiment, a sheet of thermoplastic material can be heated to soften the material and molded around the second cast. The thermoplastic material can be vacuum formed around the master with a vacuum applied to the inner surface of the thermoplastic material to cause the thermoplastic material to form to the master. In other embodiment, any other suitable material can be applied over the master to create the final socket device (FIG. 3, 161).

8) With reference to FIG. 18, the final socket device 215 can then be shipped back the prosthetist office for fitting on the patient's residual limb. (FIG. 3, 163).

Figure 4:
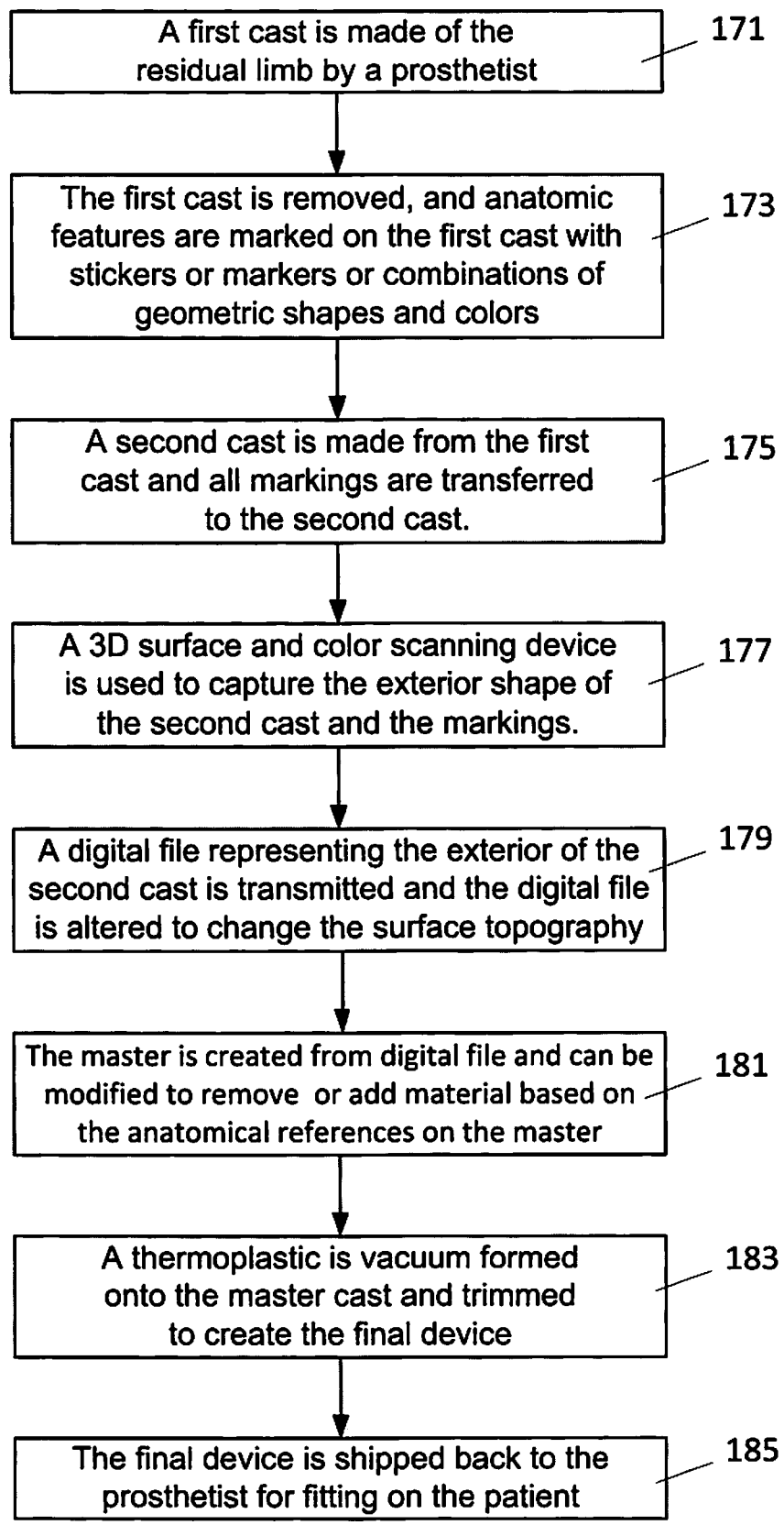
FIG. 4 illustrates a third embodiment of flowchart for processes for fabricating prosthetic sockets.

In an embodiment, a different sequence of processes can be used to make custom prosthetic sockets. For example, surface and scanning devices can be used to capture an exterior surface and markings from a second cast. The process steps for fabricating a custom prosthetic socket are disclosed with reference to FIG. 4:

1) With reference to FIGS. 6 and 7, a first cast 203 is made of the residual limb/lower limb 201 by a prosthetist in their office or other service provider (FIG. 4, 171). This can be substantially the same process described above (FIG. 2, 131, FIG. 3, 151).

2) With reference to FIG. 8, the first cast 203 is removed from the patient's residual limb or lower limb, and anatomic features are marked on the first cast (FIG. 4, 173). The markings 207 can be stickers or markers or other combinations of shapes and colors to indicate geometry and/or design intent as discussed above.

3) With reference to FIG. 10, a second cast 211 can be made from the first cast (FIG. 4, 175). The second cast 211 can be made of plaster with wet plaster soaked cotton bandages placed over all interior surfaces of the first cast. The markings 217 from the first cast indicating the anatomical features can be transferred to the second cast 217 or "master" that is substantially an exact copy of the patient's residual limb anatomy.

Figure 11:
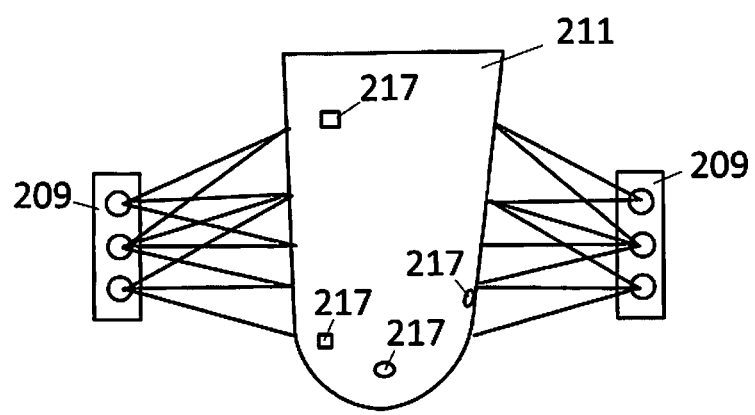
FIG. 11 illustrates an embodiment of a master with markings measured and photographed with scanners.

4) With reference to FIG. 11, a 3D scanning device 209 can be used to capture the interior shape or exterior shape of the second cast 211 and the colored markings 207 (FIG. 4, 177). The second cast 211 has an exterior surface that is convex. The important topography surfaces of the second cast 211 and markings 217 are on exterior surfaces of the second cast 211. In an embodiment, the 3D scanner(s) 209 can be placed in stationary positions around the second cast 211 or may be moved over the exterior surface topography. In other embodiments, any other suitable scanning methods can be used.

Various scanning mechanisms can be used to record the surface data. For example, a photogrammetry system can be used to capture color and depth data simultaneously. Alternatively, a time-of-flight sensor augmented with color sensor can be used to record the surface topography and color data. A structured light sensor can also be used to capture depth and color data simultaneously. The structured light sensor can also capture depth data and can be augmented with a color sensor(s) to capture the colored markings. A laser scanner can also be used to capture depth data and this surface topography data can be augmented with color sensor(s) to capture the colored markings. The scanner data and color sensor data can then be processed by a computer to create a digital representation of the second cast 211 together with the markings 217 applied to the second cast 211.

5) The digital representation of the second cast 211 and markings can be transmitted off-site and the interior surfaces can be converted into outer surfaces (FIG. 4, 179). The digital representation can match the digital representation of the residual limb of the patient. With reference to FIG. 14, in an embodiment, a recipe of "deformations" can be tally applied. For example material can be added or removed based upon the anatomic locations of bone, nerves, blood vessels, scar tissue or other body features. However, in some embodiments, some changes made idiosyncratic for the patient, based on the specifics of the patient and/or preferences of the clinician.

In one embodiment, the deformation can be described as inflations and deflations with inflations representing expanded or inflated deformations relative to the actual measured surface topographies. The deflations representing compressed or deflated deformations compared to the actual measured surface topographies. By adding inflation and deflation deformations, the pressure applied to the residual limb from the socket worn on the limb can be intentionally non-uniform. For example, the inflation and deflation deformations of the mold can increase weight bearing on soft tissue surfaces of the residual limb and decrease the pressure and force on more sensitive anatomical components of the residual limb such as nerve bundles and residual bone. Deformations can also be used to smooth the surface topography of the mold to reduce irregularities in the resulting devices such as sockets. The inflations and deflations can also be used to accommodate any intermediate devices that may be placed between the residual limb and the socket of the prosthetic such as padding, sensors, etc. These deformations can be partially or completely applied digitally, meaning that a person operating the computer aided design (CAD) device 251 can apply some or all of the deformations to the digital representation of the first cast. In an embodiment, the deformations can be applied automatically with software so that manual operation is no longer needed. The digital representation of the first cast with applied deformation modifications can be used to create a final digital representation which can correspond to or closely resemble the patient's residual limb. More specifically, the digital representation matches the residual limb with the exception of the inflations and/or deflations which are mismatched surface areas of the digital representation.

6) The final digital representation can be used to create a modified shape "master" that can be fabricated out of a plaster-like material in a central manufacturing facility (FIG. 4, 181). For example, the master can be made of gypsum using an additive manufacturing process. In one embodiment, a 3D printer that prints in a sandstone or sandstone like material can be used and the printed object is suitably similar to a plaster master made from the cast. This object is a physical representation of a modified patient's residual limb. With reference to FIG. 14, in an embodiment, the master can be fabricated with a 3D printer 253 using the CAD data. The master can be formed by creating a plurality of planar layers where each layer represents a cross section of the master. The planar layers can be sequentially bonded to the prior formed planar layer and the bonded planar layers form the master. Thus, each of the planar layers are parallel to each other.

In an embodiment, craftsmen can then apply any further idiosyncratic modifications to surface topography of this printed master. In yet other embodiments, a test socket can be made from the 3D printed master. The test socket can be formed by creating a plurality of planar layers where each layer represents a cross section of the test socket. The planar layers can be sequentially bonded to the prior formed planar layer and the bonded planar layers form the test socket. The test socket can be modified and a cast can be made from the test socket. The final socket product can then be made from a master poured into that cast.

7) With reference to FIGS. 15-17, a thermoplastic material can be vacuum-formed onto the master and trimmed to create the final socket device. In an embodiment, a sheet of thermoplastic material can be heated to soften the material and molded around the second cast. The thermoplastic material can be vacuum formed around the master with a vacuum applied to the inner surface of the thermoplastic material to cause the thermoplastic material to form to the master. In other embodiment, any other suitable material can be applied over the master to create the final socket device (FIG. 3, 161).

8) With reference to FIG. 18, the final socket device 215 can then be shipped back the prosthetist office for fitting on the patient's residual limb. (FIG. 3, 163).

Figure 12:
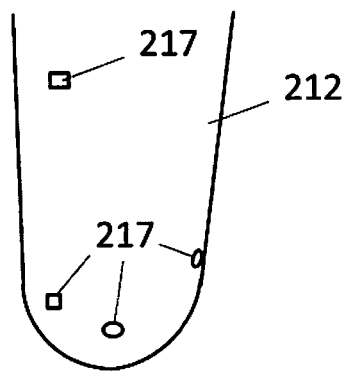
FIG. 12 illustrates an embodiment of a residual limb with markings.

In an embodiment, another sequence of processes can be used to make custom prosthetic sockets. For example, surface and scanning devices can be used to capture an exterior surface and markings from a second cast as disclosed with reference to FIG. 5:

1) With reference to FIG. 12, a residual limb 212 can be marked with markings 217 indicating the anatomical features.

Figure 5:
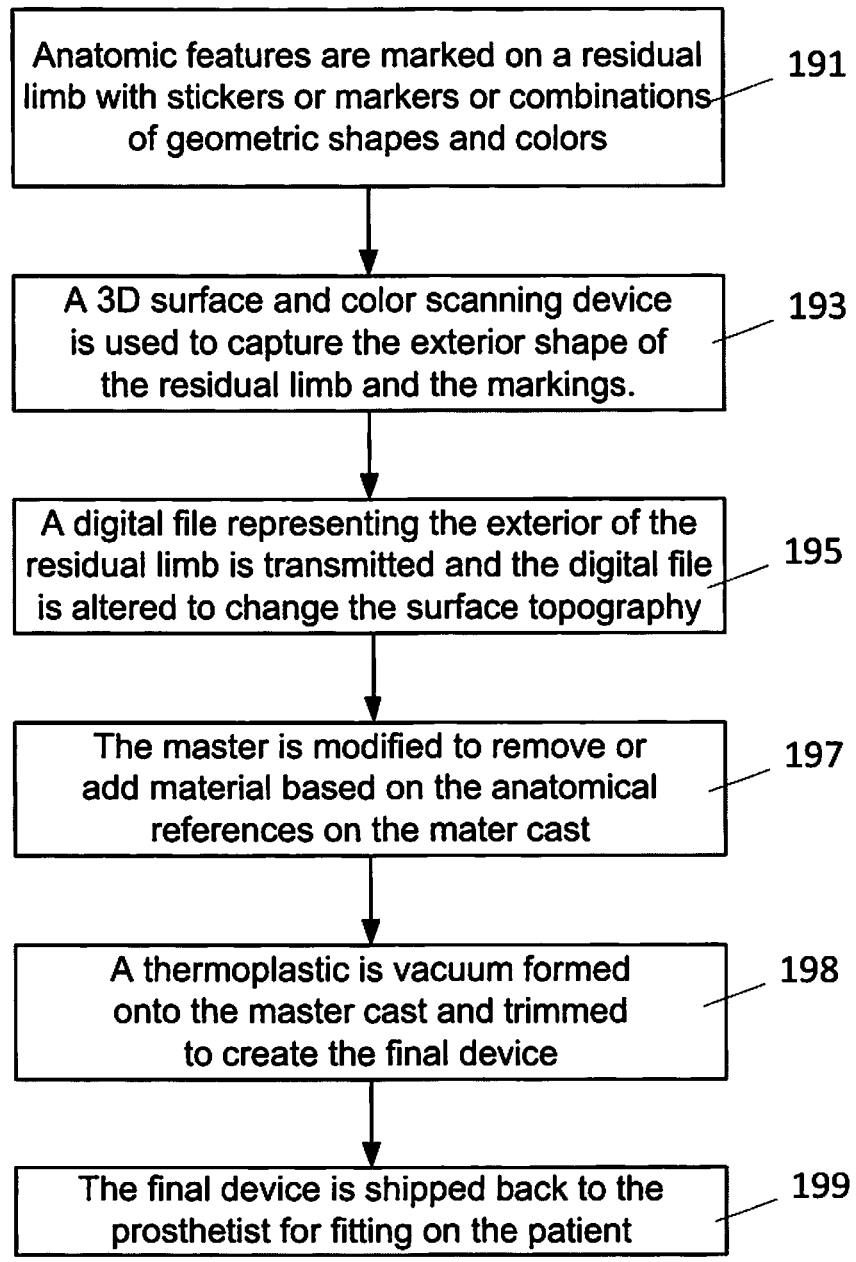
FIG. 5 illustrates a fourth embodiment of flowchart for processes for fabricating prosthetic sockets.
Figure 13:
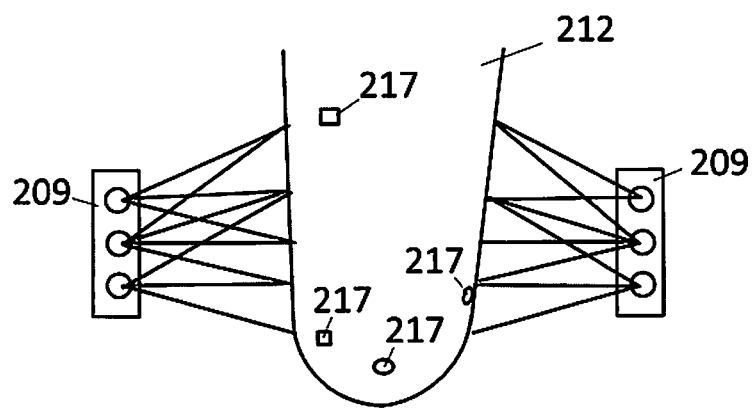
FIG. 13 illustrates an embodiment of a master or a residual limb with markings measured and photographed with scanners.

2) With reference to FIG. 13, a 3D scanning device 209 can be used to capture the exterior shape of the residual limb 212 and the colored markings 217 (FIG. 5, 193). The residual limb 212 has an exterior surface that is convex. The important topography surfaces of the residual limb 212 and markings 217 are on exterior surfaces of the residual limb 212. In an embodiment, the 3D scanner(s) 209 can be placed in stationary positions around the residual limb 212 or may be moved over the exterior surface topography. In other embodiments, any other suitable scanning methods can be used.

3) The digital representation of the residual limb 212 can be transmitted off-site and the digital representation can match the surface measurements of the residual limb of the patient. (FIG. 5, 195). With reference to FIG. 14, in an embodiment, a recipe of "deformations" can be digitally applied to the digital representation of the residual limb. The digital representation of the residual limb can be used to create a digital master design of the residual limb. A master can be fabricated using a 3D printer or any other fabrication machine. The master can be formed form a plurality of parallel planar layers of material that are fused together. Each layer can be deposited on the prior deposited layer until the master is completely formed.

4. After the master is formed, material can be added or removed from the master based upon the anatomic locations of bone, nerves, blood vessels, scar tissue or other body features. (FIG. 5, 197) However, in some embodiments, some changes made idiosyncratic for the patient, based on the specifics of the patient and/or preferences of the clinician.

5) With reference to FIGS. 15-17, a thermoplastic material can be vacuum-formed onto the master and trimmed to create the final socket device. In an embodiment, a sheet of thermoplastic material can be heated to soften the material and molded around the second cast. The thermoplastic material can be vacuum formed around the master with a vacuum applied to the inner surface of the thermoplastic material to cause the thermoplastic material to form to the master. In other embodiment, any other suitable material can be applied over the master to create the final socket device (FIG. 5, 198).

6) With reference to FIG. 18, the final socket device 215 can then be shipped back the prosthetist office for fitting on the patient's residual limb. (FIG. 5, 199).

In different embodiments, the master can be 3D printed with markings indicating pre-applied deformations with color and/or shape on the printed master, or by marking regions with a color map indicating amount of material to be removed or added from the master. Instructions for later manual modifications of the 3D printed master can be indicated through printed markings on the master. In an embodiment, the master can be 3D printed with a first material having a first color. The markings can be printed with a second material having a second color at external surfaces of the master. The second color can contrast with the first color so that the markings are easily seen when the master is fabricated. In an embodiment, the master can be formed by creating a plurality of planar layers. Each layer can form a cross section of the master. Some of the planar layers can be created from a first material having a first color and a second material having a second color. The planar layers can be sequentially bonded to the prior formed planar layer and the bonded planar layers form the master. Thus, each of the planar layers are parallel to each other.

The printed markings can correspond to annotations written on the cast or limb by the prosthetist. Those markings can be generated by the algorithms. The instructions can be regions where amount of material to be removed (deflated) or added (inflated) corresponding to colors or patterns (hashed lines). The instructions could be arrows pointing to locations for hardware assembly. Others can be thought of as well. The described methods are extensible to the creation of masters that can be used to create ankle-foot orthoses or check sockets as an intermediate steps towards the fabrication of the final product as discussed above.

The present invention is directed towards custom designed sockets for prosthetic limbs. In an embodiment, the custom sockets can be designed using a Computer Aided Design (CAD) program based upon the digital representation data from the first cast, the second cast, the master or the residual limb itself. In an embodiment, the CAD system can include a graphical user interface (GUI) that allows the prosthetic designer to easily change the design of the master or custom socket and allow these structure designs to be viewed in with any desired modifications.

When the prosthetic designer completes the designs of the master, the design data produced by the CAD software can be used to create a unique and custom fabricated master or socket. Rapid prototyping is a general category of systems that uses digital design data and software to fabricate the master or socket from various types of materials including metals and plastics. Suitable machines for 3D printing masters will be able to apply a layer of powdered stone or other powdered material down and then bind specific regions of powder using a binder fluid (acidic water) and also be able to color regions using dyes and pigments. These fabrication machines are able to create custom masters or sockets.

In order to fabricate the master or socket with the rapid prototyping machines, the CAD design data can be printed in from the unmodified master or socket design data or modified. The normal CAD design data for a component is converted into many parallel planar cross sections of vector data that extend along the length of the component. The data transmitted between the CAD software and the fabrication machine approximates the shape of the component cross sections through many connected triangular facets. Smaller facets produce a higher quality surface but require more time to calculate and can create very large manufacturing data sets. The output of the CAD design program can be a standard STL file that is an export option, similar to a JPG export or any other file format.

The primary advantage to additive fabrication rapid prototyping is the ability to create very complex shapes and geometric features such as the internal framework and exterior surfaces of a representation of a limb or portion of a limb. A light weight and strong artificial limb can be made with a rapid prototyping machine from plastic materials such as photopolymers, harder materials such as calcium carbonate or from stone such as gypsum. The rapid prototyping process can be applied to various materials including powdered stone, thermoplastics, photopolymers, metal powders, eutectic metals, titanium alloys and other materials. Similar fabrication processes are known by the names: additive manufacturing, rapid manufacturing, layered manufacturing, 3D printing, laser sintering, electron beam melting (EBM), etc. In an embodiment, the harder materials such as calcium carbonate and gypsum can be preferred because structures made of these materials are more easily modified with tools such as sand paper and/or files which can be used to remove very small amounts of material and provide smooth surfaces.

It will be understood that the inventive system has been described with reference to particular embodiments, however additions, deletions and changes could be made to these embodiments without departing from the scope of the inventive system. For example, the same processes described for designing and fabricating a prosthetic leg can also be applied to the design and construction of an artificial arm that can include a socket.

What is claimed is:

1. A method for creating a socket for a prosthetic limb comprising: making a first cast of an end portion of a residual limb of a patient; deforming the first cast by applying a compression on a lateral aspect of the first cast and applying an elongation on a ventral aspect and a dorsal aspect of the first cast such that axial displacement is prevented; placing plaster over interior surfaces of the first cast to make a second cast from the first cast; applying markings to the second cast that indicate locations of anatomic features; using a three dimensional scanning device to measure an exterior surface shape of the second cast and markings and generate scan data; creating a digital representation of the residual limb from the scan data of the second cast and markings; creating a master design from the digital representation and modifications to the digital representation; and fabricating a master from the master design.

2. The method of claim 1 further comprising:
creating the socket by molding a thermo plastic material with the master.

3. The method of claim 1 further comprising:
modifying a topography of the second cast before using the three dimensional scanning device to capture the exterior surface shape of the second cast and markings and generate scan data.

4. The method of claim 1 wherein the markings comprising a plurality of colors.

5. The method of claim 1 wherein the markings comprising a plurality of shapes.

6. The method of claim 1 wherein the markings indicate the location of a bone.

7. The method of claim 1 wherein the markings indicate the location of a nerve.

* * * * *